United States Patent [19]

Schmid et al.

[11] 4,236,413
[45] Dec. 2, 1980

[54] TESTING APPARATUS FOR TABLET-SHAPED SPECIMENS

[75] Inventors: Jürgen Schmid, Köngen; Winfried Eggert, Oberstadion, both of Fed. Rep. of Germany

[73] Assignee: Boehringer Ingelheim GmbH, Ingelheim am Rhein, Fed. Rep. of Germany

[21] Appl. No.: 21,440

[22] Filed: Mar. 19, 1979

[30] Foreign Application Priority Data

Mar. 21, 1978 [DE] Fed. Rep. of Germany ... 7808575[U]

[51] Int. Cl.³ .................................................. G01N 3/08
[52] U.S. Cl. ................................... 73/821; 33/147 L; 209/599
[58] Field of Search ........................... 73/821, 819, 78; 33/147 L, 147 N, 147 E; 209/599

[56] References Cited

U.S. PATENT DOCUMENTS 3,943,757  3/1976  Wilhelm .................................. 73/78
4,158,917  6/1979  Tagliavini ........................ 33/147 L Primary Examiner—Anthony V. Ciarlante
Attorney, Agent, or Firm—Hammond & Littell, Weissenberger & Muserlian

[57] ABSTRACT

An apparatus is provided for the sequential combined measurement of height (or thickness) and compression strength of successive tablet specimens. The apparatus comprises a specimen-fed chute for depositing the specimens on a conveyor for oriented transport to a measuring station where the tablet height and then its compressive strength are determined. The conveyor is provided with cleansing means for removing the tablet remnants from the compression measurement.

2 Claims, 5 Drawing Figures

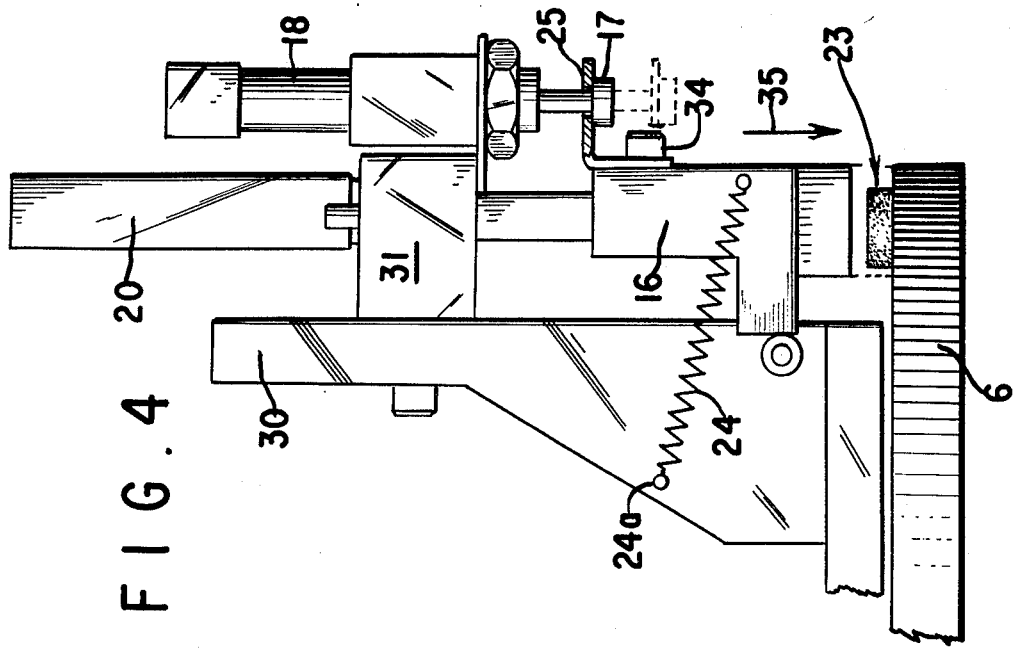
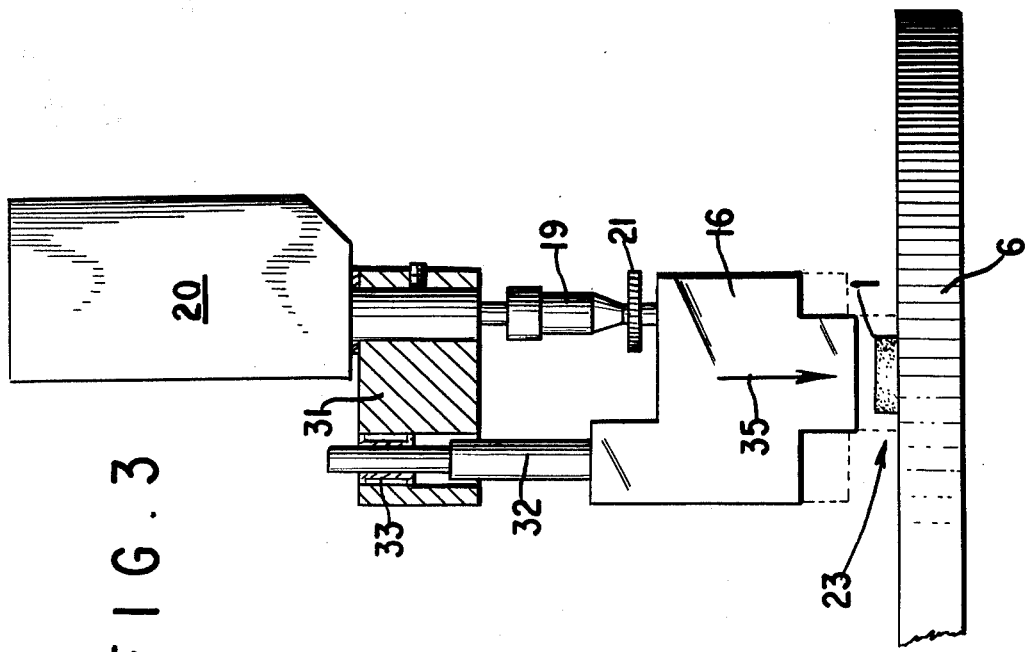

TESTING APPARATUS FOR TABLET-SHAPED SPECIMENS

FIELD OF THE INVENTION

This invention relates to tablet manufacturing, and more particularly to improvements in or relating to an apparatus for the rapid measurement of statistically significant values of thickness and compression strength of tablet-shaped selected specimens from tablet-making operations.

The apparatus hitherto known has merely permitted either individual meansurement of the compressive strength or the thickness of tablet specimens. A further disadvantage of such known apparatus is that specimens have to be manually introduced into each measuring device for each measuring operation. It has therefore not been possible to rapidly analyze a substantially significant test group from a tablet batch.

THE INVENTION

It is an object of the present invention to provide improved test apparatus of the kind mentioned. According to the invention, there is provided an apparatus for the combined rapid measurement of thickness and compression strength of tablet-shaped specimens. The apparatus comprises a conveyor; feeding means operatively associated with the conveyor and adapted to receive selected said specimens and to pass those within a predetermined range of weight to the conveyor, said feeding means being adapted to orient said specimens to lie flat on the conveyor; a combined thickness and compression-strength measuring station disposed downstream of said feeding means, fitted with a thickness measuring gauge adapted to first measure the height of a said specimen oriented on the conveyor, and a compression strength measuring device adapted to compress said specimen to failure and measure its strength, and a cleaning device at said station adapted to remove from the station the remnants of the failed specimens.

In the single apparatus according to the invention, the introduction and conveyance of the selected specimens, the combined measurement of their thickness and compression strength and the cleaning of the entire system takes place rapidly and fully automatically. It is thus possible to effect measurements of the specimens at a rate of up to approximately 25 specimens per minute.

While it is possible for the conveyor to take the form of an elongated conveyor belt, with said feeding means, testing station with the thickness measuring device and compression-strength measuring device spaced along the belt, it is preferable in the interests of reducing the size of the apparatus for the conveyor to comprise a rotatable disc. Thus the components may be disposed around the disc, which effects a considerable saving in space and simplifies the positioning and actuation of the measuring and cleansing components.

In a preferred embodiment, the feeding means includes a downwardly tapering guide chute mounted above the rotatable disc conveyor, a movable gate member adapted in one operative position to permit passage of a specimen through the chute and onto the conveyor, and in another operative position to reject or divert a said specimen, and means adapted to move and preferably to vibrate said chute in order to overturn any said specimen landing on its side on the conveyor so as to orient it to lie flat. This preferred arrangement is of particular importance in maximizing the advantages obtained by the invention. The movable gate is conveniently actuated into one of its two operative positions by a corresponding electrical pulse obtained from weighing means which serve to weigh each specimen or a statistically determined random selector. In the weight-actuated embodiment, the specimen falls within the given weight range, the gate moves into its first mentioned operative position to allow the specimen through the chute. If the specimen lies outside the given weight range, then the gate is actuated into its other operative position, in which position the respective specimen is discharged from the feeding means, for example to a receptacle for tablets to be disposed of. The random selector chooses specimens representative of the batch for testing and thus determines the need for adjustment of the tabletting presses.

Certain tablet specimens may have a diameter-thickness ratio of such a value that they may be prone to landing and remaining on the conveyor on their edge. This does not permit the thickness measuring gauge to operate properly, and therefore the said displacing or vibrating means are provided to orient the specimen so as to cause it to lie flat. The chute feeding means can be provided with a special turned edge to engage the specimens should the specimen fall in such a way that, if circular, it tends to roll on the conveyor. Should it, however, fall onto the conveyor in such a way that its general plane lies at right angles to the direction of the conveyor at the landing point, then engagement with a side of the feeding means will tend to flip it into its flat position. It should be noted that in either case it is desirable that the spacing between the lower edge of the feed chute and the conveyor be greater than the radius of circular specimens. Means may, for example, be provided to adjust this spacing manually according to dimensions of the specimens being tested.

The apparatus will preferably include a cam or other guide means adapted to guide the tablet specimen on the conveyor to said measuring station for determination of the thickness and compression-strength measuring device. In this way the conveyor can serve to guide the specimen into the station position in which said measurements are to take place. To ensure that the specimen stops in the right place, there may be provided a stop member adapted to stop a said specimen at the station. However, to ensure that the measurement is not affected by impingement on the stop member of the measuring instruments, the conveyor preferably includes a resiliently mounted brake adapted to stop the conveyor when said specimen reaches the measuring station, and then to move the conveyor backwards by a small distance to clear the specimen from the stop member.

In a preferred embodiment of the invention the brake includes a brake shoe acting on a disc and mounted for limited circumferential movement therewith and a tangentially mounted spring adapted, on arrest of the disc, to deform and by its resilience rotate the disc backwards by said small distance to clear the specimen.

Since testing the tablet specimens for compression strength requires testing to destruction, the measurement of the thickness of the specimens is carried out first. Then, without having to convey the specimen under test from the thickness measuring gauge to the compression-strength measuring device by mounting these units at the first station, both tests are carried out on the specimen at the same location. The thickness measuring station includes a height measuring device which is preferably mounted directly above the compression-strength measuring device. Because of the destroyed tablets, the conveyor at the measuring station is strewn with tablet remnants which must be cleared or cleansed to ensure accurate measurement.

Various methods are possible for ensuring that the specimen is properly located at the measuring station. Thus the arrival of the specimen at the measuring station is determined by the amount that the conveyor moves. Alternatively, sensing means can be provided at or near the measuring station together with means operable in response to said sensing means to arrest the conveyor on sensing of a specimen reaching the measuring station. The latter embodiment, therefore, provides for automatic termination of the movement of the conveyor when the specimen under test reaches the measuring station The cleaning device comprises any number of cleaning means or combination thereof. For example, a pivotable lever having a cleaning head, preferably a brush, may be adapted to pass over the conveyor at the measuring station, and alternatively or additionally the cleaning device may include a blower adapted to blow said remains or remnants from the conveyor and/or a dust suction device adapted to suck the remains of said specimens from the conveyor. The cleaning device is mounted adjacent to said conveyor to span the measuring station by its cleansing action.

DETAILED DESCRIPTION OF THE INVENTION

Figure 1:
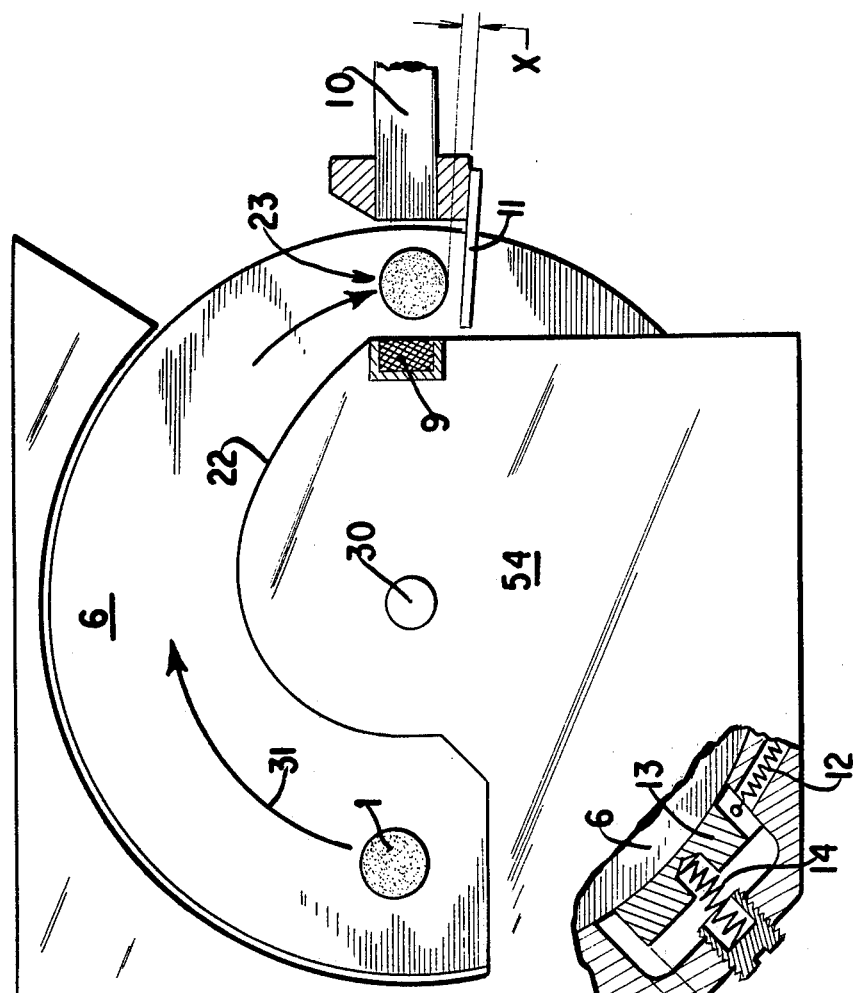
Figure 2:
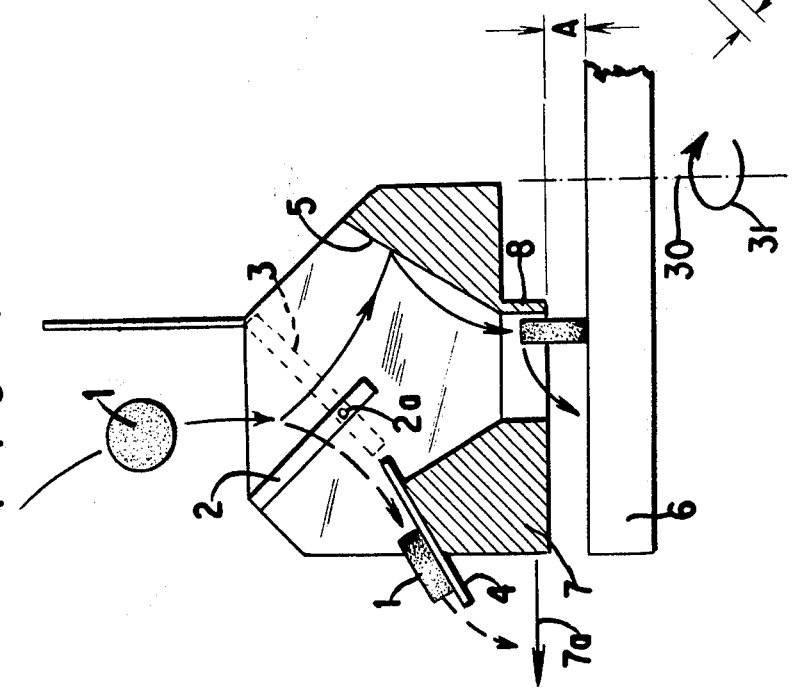
Figure 5:
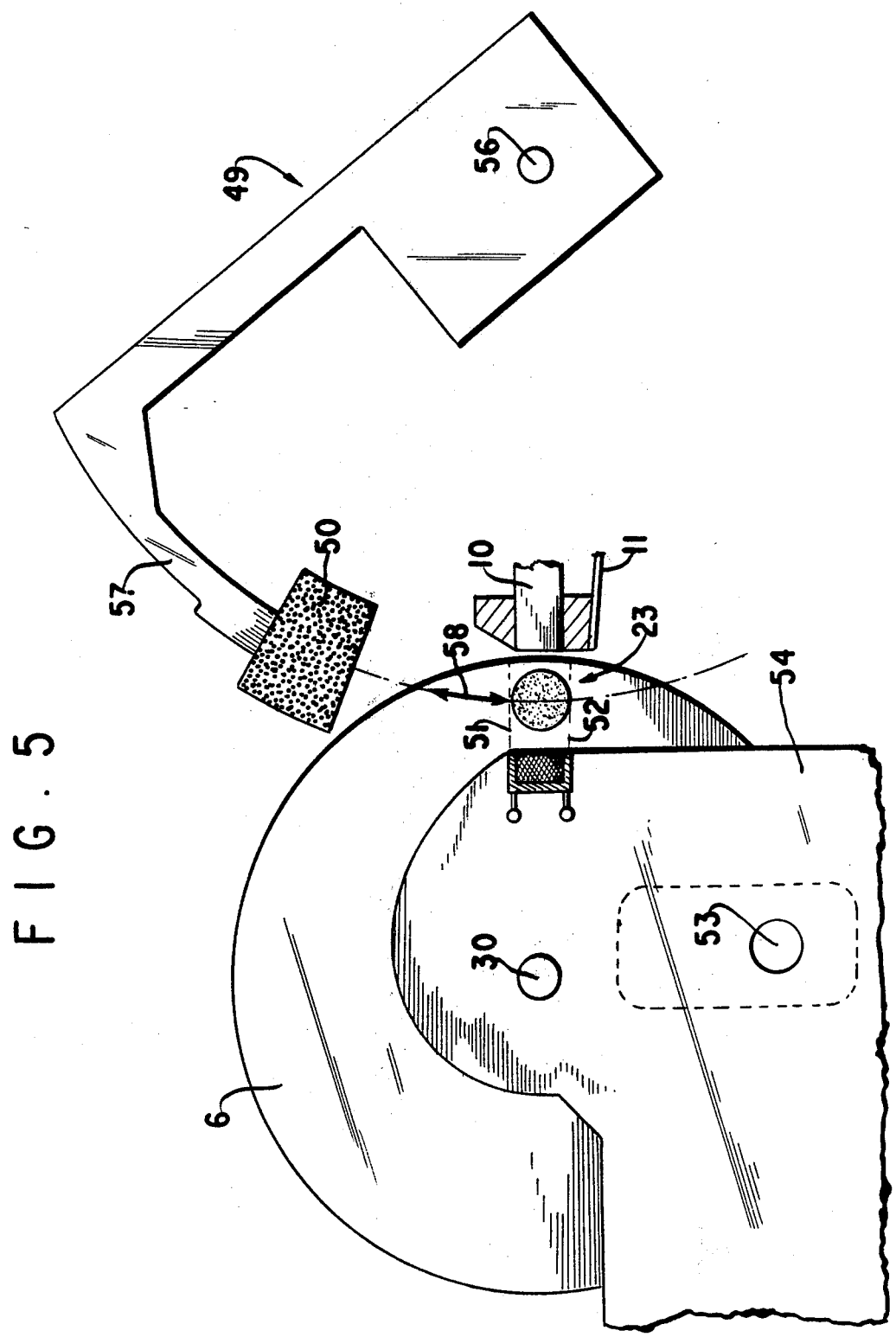

In order that the invention may be readily understood, an embodiment thereof will now be described by way of example with reference to the accompanying drawings in which:

FIG. 1 is a radial sectional view through an embodiment of the feeding means,

FIG. 2 is a partly cut-away plan view of the apparatus in accordance with the invention, FIG. 3 is a sectional view of the thickness measuring gauge, FIG. 4 is a circumferential view of the thickness measuring gauge, and FIG. 5 is a plan view showing the compression-strength measuring device and the associated cleaning means Referring first to FIG. 1, there is shown a feeding means comprising a chute body 7 whose internal wall 5 tapers downwardly. At the mouth of the chute there is provided a gate 2 hingedly mounted to the chute body 7 at the pivot point 2a. In the position shown in bold lines the gate 2 is adapted to direct the specimen tablet 1 to pass onto the internal wall 5 and then onto the conveyor 6. However, the gate is associated with further control means (not shown) which serve to pivot the gate into the position indicated by broken lines shown at 3 in the case that the tablet does not lie within the predetermined range of weight or is not of the group to be tested. In this case, the tablet is prevented from reaching the conveyor and slides down a separate chute 4 to a receptacle (not shown).

The conveyor 6 is in the form of a rotating disc having an axis of rotation designated 30 and which is rotating in the direction of the arrow 31. Should the tablet 1 land on the disc 6 in the upright position shown, then it could simply roll along the disc as the disc rotates and not leave the feeding means. To prevent this, the chute is vibrated in the radial direction i.e. that of the arrow 7'. Since the distance A is greater than the radius of the tablet, the tablet is overturned to lie flat on the conveyor 6 in which position it leaves the feeding means. To this end the tablet is engaged by the lowermost edge 8 of the chute body 7 which causes the tablet to tip over into the flat position on conveyor disc 6. The distance A of lip 8 over disc 6 may be adjusted manually so as to suit different sizes of specimens.

Turning now to FIG. 2, the specimen 1 is seen traveling on the conveyor in the direction 31 towards the measuring station 23. In order to ensure that the specimen 1 arrives at the correct radial spacing from the axis 30, there is provided a cam surface 22 against which the specimen 1 impinges and by which it is directed to station 23.

The specimen 1 is carried by the conveyor 6 until it abuts stop 11 which prevents further circular movement. The disc 6 can be preprogrammed to stop when the specimen reaches stop 11, or sensing means such as an optical or mechanical device may be provided so that when stop 11 is reached by the specimen the conveyor is automatically stopped.

The preferred means for stopping the conveyor are shown in the bottom left hand corner of FIG. 2. The brake shoe 13 is urged against conveyor disc 6 by a compression spring 14. When the brake shoe 13 comes into contact with the disc 6, it will itself tend to move the circumferential direction by virtue of the momentum of the disc. The shoe 13 is permitted to advance by a small distance X against the resilience of a tangential spring 12. Thus when the conveyor 6 is arrested from forward motion, the spring 12 thus under tension will cause disc 6 to be driven backwards by the small distance X, which as will be seen at the measuring station 23 causes the specimen 1 to retreat by the same distance X from the stop lever 11. The distance X is determined when the shoe abuts against abutment 15.

The thickness gauge at measuring station 23 is shown in greater detail in FIGS. 3 and 4. It comprises a support member 30 on which is mounted a bridge portion 31. The bridge portion mounts the operative parts of the measuring station. These latter parts comprise an optoelectric measuring feeler 20 which has a movable plunger 19 which is fixed to the specimen engaging slide 16 by means of a set screw 21. In order to calibrate the measuring feeler 20, the slide is urged into the position shown in dash-dot lines in FIG. 3, so as to abut the conveyor disc 6, and this constitutes a zero position.

The slide 16 is guided for vertical parallel-wise movement in the bridge 31 by means of a guide rod 32 extending therefrom and being received within a guide passage 33. Vertical movement up and down of the slide 16 is obtained by means of compressed air cylinder 18 having a piston rod 17 extending therefrom and engaging in a bracket 25 which is fixed to slide 16 by means of bolt 34. Thus when the cylinder rod 17 extends from cylinder 18, the slide 16 moves down under its own weight onto the specimen 1 lying directly thereabeneath. The arrow 35 shows the direction of this movement.

When the slide 16 abuts and lies on the specimen 1, a reading for the thickness of specimen is obtained from the feeler 20. The readings are preferably recorded on a recording device (not shown). They may be used to control the tablet manufacturing apparatus.

Spring 24 fixed in a pivotable mounting 24a serves as a counter balance for the slide 16.

When the thickness of specimen has been measured, its compression-strength is then determined. The device for achieving this determination is shown diagrammatically in FIGS. 2 and 5. It comprises a press ram 10 at measuring station 23 which moving to the left is seen in the Figures mentioned, serves to compress the specimen 1 against the compression measuring lever 9. Lever 9 is associated with one or two strain-gauge dynamometers and associated electronics (not shown), which serve to measure the pressure applied to the specimen by ram 10. Ram 10 may, for example, be actuated pneumatically. The applied pressure is steadily increased until the tablet shatters, at which point the failure pressure is recorded on a suitable apparatus (not shown).

Preferably, two dynamometers are used which are attached to the measuring lever in opposite senses. The first dynamometer provides, as it were, a fulcrum for the measuring lever 9, and the upper part of the measuring lever then presses on the second dynamometer in the opposite direction. The pressure to which the specimen is subjected is obtained from the difference between the pressure values measured on the two dynamometers. This is a conventional arrangement.

FIG. 5 shows an embodiment of the invention clearly illustrating the means for cleaning the remains of the compression-destroyed specimen from conveyor 6 at test station 23. A rocking lever 49 is mounted at the plane of conveyor disc 6 but adjacent thereto, and is pivoted about axis 56. Lever 49 includes an arcuate portion 57 which mounts at its free end a brush head 50. The brush head 50 is adapted for forward and backward movement in the direction indicated by arrow 58 at station 23 between the two main parts of the compression-measuring instrument. The height gauge 16 and stop lever 11 are withdrawn to permit movement of the head so as to brush off from the conveyor the fragments of destroyed specimen remaining thereon.

As a result of the stop lever swinging back, the presurized air remaining in the cylinder of the ram 10 is released and directed to the space 51, 52 so as to provide for additional removal of fragments. Furthermore, in the housing 54 there is provided additionally an extractor in the bore 53 which serves to continuously suck any remaining dust tending to accumulate on the conveyor. Lever 49 is externally actuated and its operation is keyed to the measuring sequence following after the compression-measurement of a first specimen and before the positioning of the next specimen at measuring station 23.

It will be seen that the apparatus provided permits by the operative association of the component parts rapid measurment of the thickness and compression strength of tablets such that a statistically relevant number of tests may be made in a very short time.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An apparatus for the combined measurement of the thickness and the compression strength of tablet-shaped specimens comprising a conveyor including a rotatable disc, feeding means for orienting said specimens on said conveyor, a specimen measuring station located on said conveyor downstream from said feeding means and equipped with means for thickness and compression strength measurement, said station including cleaning means for removing and cleaning from said station substantially all remnants of specimens from the compression strength measurement means, said measurement and cleaning means being serially activated, said measuring station further including a stop member adapted to stop said specimen on said conveyor at said station, and said conveyor also including a resiliently mounted brake adapted to stop the conveyor when said specimen reaches said stop member and then remove the conveyor backwards a small distance sufficient to clear said specimen from said stop member.

2. The apparatus of claim 1, wherein said disc is fitted with a resiliently mounted brake and includes a brake shoe acting on said disc and mounted for limited circumferential movement therewith, and a tangentially mounted spring adapted, on arrest of said disc, to deform and by its resilience rotate the disc backwards by a small amount in roder to clear the test specimen from the brake actuating the stop means.

* * * * *